(12) United States Patent
Katsuki et al.

(10) Patent No.: US 8,784,624 B2
(45) Date of Patent: Jul. 22, 2014

(54) ENZYME ELECTRODE

(75) Inventors: Koji Katsuki, Kyoto (JP); Konomu Hirao, Kyoto (JP); Kenji Nagakawa, Kyoto (JP); Masashi Okamoto, Kyoto (JP); Yoshiaki Fujinawa, Kyoto (JP)

(73) Assignee: Arkray, Inc., Kyoto (JP)

( * ) Notice: Subject to any disclaimer, the term of this patent is extended or adjusted under 35 U.S.C. 154(b) by 1130 days.

(21) Appl. No.: 12/309,222

(22) PCT Filed: Jul. 11, 2007

(86) PCT No.: PCT/JP2007/063863
§ 371 (c)(1),
(2), (4) Date: Mar. 29, 2010

(87) PCT Pub. No.: WO2008/007719
PCT Pub. Date: Jan. 17, 2008

(65) Prior Publication Data
US 2010/0187107 A1    Jul. 29, 2010

(30) Foreign Application Priority Data
Jul. 12, 2006  (JP) ................................. 2006-191734

(51) Int. Cl.
*G01N 27/327*  (2006.01)

(52) U.S. Cl.
USPC .............. 204/403.14; 204/403.01; 422/82.01; 422/98

(58) Field of Classification Search
USPC .............. 204/403.01–403.15; 205/777.5, 778, 205/792; 435/4–40.52; 422/68.1–98; 436/62–71, 500–548
See application file for complete search history.

(56) References Cited

U.S. PATENT DOCUMENTS

| | | | |
|---|---|---|---|
| 4,732,660 A * | 3/1988 | Plowman et al. | 204/265 |
| 4,970,145 A | 11/1990 | Bennetto et al. | |
| 5,160,418 A | 11/1992 | Mullen | |
| 5,227,042 A * | 7/1993 | Zawodzinski et al. | 204/403.1 |
| 5,231,028 A | 7/1993 | Mullen | |
| 5,476,776 A * | 12/1995 | Wilkins | 435/176 |
| 5,529,676 A * | 6/1996 | Maley et al. | 204/409 |
| 5,643,721 A * | 7/1997 | Spring et al. | 435/6.16 |
| 6,764,581 B1 | 7/2004 | Forrow et al. | |
| 2004/0197935 A1 | 10/2004 | Forrow et al. | |
| 2006/0258959 A1* | 11/2006 | Sode | 600/584 |
| 2007/0034512 A1* | 2/2007 | Yamaoka et al. | 204/403.01 |

FOREIGN PATENT DOCUMENTS

WO   WO 2005043146 A1 *  5/2005

OTHER PUBLICATIONS

Wang et al., "Zeolite containing oxidase-based carbon paste biosensors," Journal of Electroanalytical Chemistry, Vo. 404, No. 2, Mar. 21, 1996, pp. 237-242.

* cited by examiner

*Primary Examiner* — Susan D Leong
(74) *Attorney, Agent, or Firm* — Rader, Fishman & Grauer PLLC

(57) ABSTRACT

The present invention relates to an enzyme electrode including: a carbon particle; a metal particle held on the carbon particle, the metal particle having a catalytic activity against a redox reaction; a redox enzyme. The enzyme electrode of the present invention further includes a high-resistance particle enhancing an electrical resistance, the high-resistance particle being chemically stable. The high-resistance particle contains an inorganic substance, for example. The inorganic substance is aluminum oxide or smectite, for example.

20 Claims, 2 Drawing Sheets

ENZYME ELECTRODE

TECHNICAL FIELD

The present invention relates to an enzyme electrode containing a carbon particle holding a metal particle such as a noble metal having a catalytic activity, and a redox enzyme.

BACKGROUND ART

Some enzyme electrodes can obtain a response correlated with the concentration of a ground substance in the manner of current measurement using the redox enzyme. An example thereof is obtained by fixing the redox enzyme to platinized carbon (for example, see Patent Document 1 to 3). The enzyme electrode using the platinized carbon advantageously eliminates the need for an electron mediator.

Enzyme electrodes described in Patent Document 1 to 3 are obtained by immobilizing a redox enzyme to a porous layer formed by bonding a platinized carbon particle using a binder. The platinized carbon particle is obtained by holding platinum on the surface of the carbon particle. Platinum is held on the carbon particle as a metal particle, a platinum oxide particle or an oxide particle obtained by oxidizing the surface of a platinum particle. Glucose oxidase (GOD) is disclosed as the redox enzyme.

The enzyme electrode may be obtained by forming the porous layer as a surface layer on the surface of a conductive supporting member. As the conductive supporting member, carbon paper or a web of a carbon fiber of a filament is used.

In the enzyme electrodes described in Patent Documents 1, 2, a synthetic resin, preferably polytetrafluoroethylene is used as the binder.

On the other hand, in the enzyme electrode described in Patent Document 3, as the binder, there is not used a binder (that is, a high-melting point fluorocarbon resin or a hydrophobic resin, for example, polytetrafluoroethylene) which needs a high temperature for sintering processing but a water-soluble or water dispersible binder, for example, gelatin in order to realize the mass production of the enzyme electrode.

The present inventors have experimentally produced a glucose dehydrogenase (GDH) platinized carbon enzyme electrode using, as a binder, a solid polyelectrolyte used much for an ion-exchange membrane or the like in the field of a fuel cell. There was used NAFION (registered trademark) which was particularly preferable as the solid polyelectrolyte and was developed by Du Pont Company of United States of America. Since NAFION has high endurance and chemical stability, NAFION is a fluorine sulfonic acid polymer electrolyte which is stronger in the operation at a high temperature than of other electrolysis film. Similarly, a paraffin wax as a petroleum wax was used as a binder, and an enzyme electrode was experimentally produced. Neither NAFION nor the paraffin wax needs the sintering of a high temperature.

However, when voltammetric measurement or amperometric measurement was carried out using the GDH platinized carbon enzyme electrode as an anode electrode, and using glucose of an enzyme ground substance as a measuring object, accordingly, the output characteristics of a measurement sensor including the GDH platinized carbon enzyme electrode were different and the reproducibility was low (not stabilized) whenever a measurement sensor was experimentally produced.

Therefore, in a measurement using a voltammetric method or an amperometric method when carrying out glucose measurement using the GDH platinized carbon enzyme electrode, the stable operation may not be able to be carried out as it is, or the operation condition as the enzyme electrode may be mostly limited. As a result, the condition range of the appropriate operation may become very narrow.

Patent Document 1: WO87/No. 07295 pamphlet
Patent Document 2: Japanese Patent Application National Publication (Laid-Open) No. 02-501679
Patent Document 3: Japanese Patent Application Laid-Open (JP-A) No. 02-99849

DISCLOSURE OF THE INVENTION

It is an object of the present invention to stably and reproducibly carry out electrochemical measurements such as voltammetric measurement and amperometric measurement in an enzyme electrode containing a carbon particle holding a catalyst metal such as platinum, and a redox enzyme.

The present invention relates to an enzyme electrode including: a carbon particle; a metal particle held on the carbon particle, the metal particle having a catalytic activity against a redox reaction; and a redox enzyme. The enzyme electrode of the present invention further includes a high-resistance particle enhancing an electrical resistance, the high-resistance particle being chemically stable.

Effect of the Invention

Since the enzyme electrode according to the present invention includes the high-resistance particle enhancing the electrical resistance, the high-resistance particle being chemically stable, the enzyme electrode can stably and reproducibly carry out the electrochemical measurements such as the voltammetric measurement and the amperometric measurement.

BEST MODE FOR CARRYING OUT THE INVENTION

Figure 1:
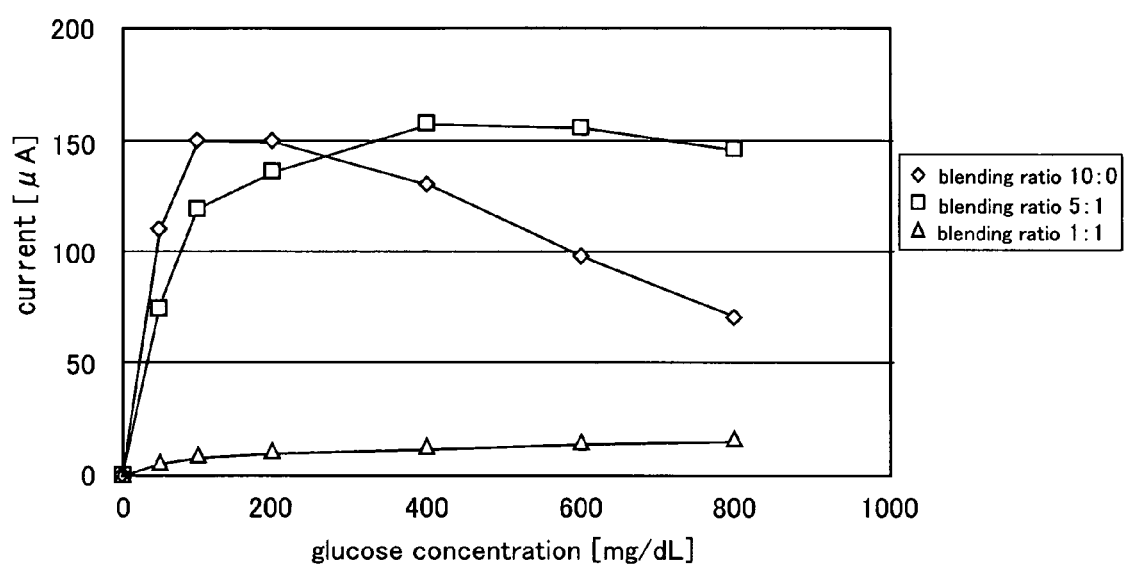
FIG. 1 is a graph showing the measurement results of current values in example 3.

An enzyme electrode according to the present invention is mainly used for a clinical use, for example, for the detection or quantitative measurement of a ground substance in a sample. Examples of clinical samples include blood, serum, plasma, urine, sweat, tear and saliva. Examples of the ground substances include glucose. The enzyme electrode of the present invention can be further used for an nonclinical use, for example, the surveillance of fermentation, control of industrial processes and environmental surveillance (for example, the suppression of the outflow of a fluid and gas and contamination), the test of food, and veterinary medicine.

The enzyme electrode of the present invention contains a carbon particle, a metal particle, a redox enzyme, and a high-resistance particle.

The carbon particle ensures the conducting properties of the enzyme electrode and holds the metal particle or the like.

The carbon particle preferably used in the present invention is an activated carbon, graphite, carbon black or diamond-like carbon particle. The carbon particle is used, which has a particle size of 3 to 150 nm, for example, and more preferably 3 to 50 nm.

The redox enzyme catalyzes the oxidation or reduction reaction of the ground substance. The redox enzyme is selected according to the kind of the ground substance. For example, when the ground substance is glucose, a glucose dehydrogenase is preferably used. For example, a coenzyme-dependent enzyme can be used for the glucose dehydrogenase. Examples of coenzymes include flavin adenine dinucleotide (FAD), pyrroloquinoline quinone (PQQ), nicotinamide adenine dinucleotide (NAD+), nicotinamide adenine dinucleotide phosphate (NADP+), heme, and an iron-sulfur cluster. Preferably, the glucose dehydrogenase FADGDH using FAD as the coenzyme is used in view of the size of an electric output.

The blending amount of the redox enzyme in the present invention will be widely changed depending on a specific enzyme or enzyme mixture to be used. The inventors' experiment reveals that the blending amount which corresponds to an electrode surface of 10 to 500 ug/cm$^2$ in FADGDH should be satisfied, and preferably 100 to 200 μg/cm$^2$.

The metal particle, which has a catalytic activity against a redox reaction, is held on the carbon particle. Typical examples of the metal particle capable of being used in the present invention include particles made of noble metals such as platinum (Pt), rhodium (Rh), gold (Au), silver (Ag), palladium (Pd), ruthenium (Ru), iridium (Ir) and osmium (Os). These noble metals may be used alone, or a plurality of kinds thereof may be used together. Preferably, platinum is used alone, or platinum and a noble metal of the other kind are used together. As the metal particle, the oxide of the exemplified noble metal and the noble metal particle having a surface subjected to oxidation treatment, other than the noble metal such as indium (In), rhenium (Re) and copper (Cu) and an oxide thereof can be also used as long as the metal particle has the catalytic activity against the redox reaction. Even when ones other than the noble metal are used, they are preferably used together with the noble metal such as platinum.

Since the metal particle is held on the carbon particle, the particle size thereof is made to be a size suitably held on the carbon particle, for example, a size of a colloid level of 1 nm to 20 μm, and preferably 1 to 4 nm.

The amount of the metal particle held on the carbon particle is made to be 0.1 to 60 parts by weight, for example, relative to 100 parts by weight of the carbon particle. This reason will be described later. When the amount of the metal particle held on the carbon particle is less than 0.1 parts by weight, the level of an output signal is extremely low for being measured except the use of a measuring device having extremely high sensitivity. On the other hand, when an expensive noble metal such as platinum is used in the case where the amount is more than 20 parts by weight, the amount becomes noneconomic and does not substantially provide added profits in view of the increase in response or sensitivity. Preferably, the amount of the metal particle held on the carbon particle is made to be 0.5 to 40 parts by weight relative to 100 parts by weight of the carbon particle.

The high-resistance particle is added in order to enhance the electrical resistance of the enzyme electrode. The content of the high-resistance particle in the enzyme electrode of the present invention is made to be 0.1 to 99 parts by weight, preferably 5 to 80 parts by weight, and more preferably 20 to 60 parts by weight relative to 100 parts by weight of the carbon particle, for example. The high-resistance particle having a particle size of 3 to 150 nm, for example, is used.

Herein, in a fuel cell using glucose as fuel, the obtained electromotive force (open circuit voltage) is about 0.4 V in a single cell, the low electromotive force is obtained. In order to enhance the electromotive force in this fuel cell, enhancement in efficiency and reduction in voltage drop loss in a path in which electrons taken out by the glucose oxidation reaction of fuel are transmitted to an electrode are made to be very important in view of increasing the electromotive force of a battery.

On the other hand, the enzyme electrode of the present invention contains the high-resistance particle, and thereby the voltage of the battery when a current flows (in loading) is reduced as much as possible by consciously increasing the voltage drop loss in the path in which the electrons are transmitted to the electrode. That is, the enzyme electrode of the present invention consumes the electromotive force in the cell reaction in the internal resistance of the electrode. The electromotive force may be generated due to the oxidation reaction of the ground substance using the metal particle such as platinum as the catalyst. That is, the enzyme electrode of the present invention uses IR drop like phenomenon caused by enhancing the internal resistance to suppress the instability of an electrode output.

On the other hand, the high-resistance particle has to be chemically inactive in order not to block the function as the enzyme electrode, that is, the enzyme reaction caused by the redox enzyme. That is, the high-resistance particle capable of being used in the present invention is required to enhance the electrical resistance of the electrode and be chemical inactive.

The resistance required to the high-resistance particle is determined by the size of the electrical resistance of the enzyme electrode when the enzyme electrode does not contain the high-resistance particle, the size of the electrical resistance of the enzyme electrode finally required, or the content in the enzyme electrode, or the like. For example, when the electrical resistance in the enzyme electrode when the enzyme electrode does not contain the high-resistance particle is 1 kΩ or more, and when the size of the electrical resistance of the enzyme electrode finally required is 30 kΩ or more, the high-resistance particle having an electrical resistance of 1 MΩ or more is used.

As the high-resistance particle, an inorganic substance is preferably used. As the inorganic substance for the high-resistance particle, aluminum oxide, silicate or an inorganic substance primarily containing them can be used, for example. As the inorganic substance primarily containing aluminum oxide, AEROSIL (manufactured by Degussa AG, registered trademark) is preferably used. A clay mineral (smectite) can be used as the inorganic substance primarily containing silicate. Of course, as the high-resistance particle, an organic substance such as latex can be also used in addition to the inorganic substance.

The enzyme electrode of the present invention contains a binder basically. This binder bonds the carbon particles each other. The binder may be a conventional hydrophobic synthetic resin having a high-melting point, for example, a fluorocarbon resin binder of 10 parts by weight or less such as polytetrafluoroethylene. In addition, a water-soluble or water dispersible binder, for example, hydroxyethyl cellulose or gelatin can be also used. When a petroleum wax or a fluorine sulfonic acid polymer is selected from them as the binder, the small amount of the binder causes a large bonding effect, and thereby the uniformity of a dispersion state can be desired. In particular, the fluorine sulfonic acid polymer is preferable in view of enhancement in proton mobility on the surface of the electrode.

Any of a paraffin wax, a microcrystalline wax and a petrolatum can be used as the petroleum wax capable of being used in the present invention. The paraffin wax is preferable since the paraffin wax is easily treated in solid form at normal temperature and the enzyme electrode can be molded, shaped or printed. As the fluorine sulfonic acid polymer capable of being used in the present invention as another embodiment, NAFION (registered trademark) developed and sold as a solid polyelectrolyte for a fuel cell material by Du Pont Company of United States of America is preferable. The amount of the binder to be used is made to be 5 to 100 parts by weight, and preferably 20 to 50 parts by weight relative to 100 parts by weight of the dry weight of the total of a carbon powder, metal powder and redox enzyme.

The enzyme electrode of the present invention may be formed on the surface of a supporting member. In this case, any of the supporting members may have insulative or conducting properties.

As the supporting member having insulative properties, commercially available engineering plastics such as polyethylene terephthalate, polyimide, polystyrene, JURACON (Polyplastic Company, registered trademark), for example, can be used. The shape of the supporting member is formed into a film or rod shape, for example. Of course, the shape of the supporting member, which is not limited to the exemplified shape, can be variously changed according to the object.

On the other hand, as the conductive supporting member, for example, a conductive carbon paper, a carbon fiber web, or a plate-shaped or rod-shaped metal (for example, platinum) can be used. When the conductive supporting member is used, this supporting member may function as a lead for extracting the output from the enzyme electrode.

The enzyme electrode according to the present invention is used as, for example, a part of a biosensor or the like. However, known various constitutions can be adopted as a method for extracting the output from the enzyme electrode of the present invention, and the method is not particularly limited.

The enzyme electrode of the present invention can be formed by molding, shaping or printing the mixture having the aimed composition.

The mixture is formed in the carbon particle holding, for example, the metal particle, the high-resistance particle, the redox enzyme and a liquid suspension medium obtained by adding the binder as required.

As the liquid suspension medium, water, an amphiphilic solvent or an organic solvent can be used, for example. Thus, the carbon particle, the high-resistance particle and the redox enzyme can be substantially homogeneously mixed by mixing them in the liquid suspension medium. However, when the organic solvent is used, for example, ethanol, cyclohexane or dichloromethane are preferably used so that substantial inactivation of the enzyme is not generated.

The mixture is molded or shaped by, for example, pressing after adding a suspension into a forming die. The enzyme electrode is obtained by evaporating the liquid suspension medium by drying after molding the mixture.

When the enzyme electrode is formed by molding or shaping, the enzyme electrode is formed into the aimed shape, capacity or area such as a pillar shape of a rod shape or the like, a tablet shape, and a cylindrical shape according to the shape of the forming die by using a core as required. The supporting member may be buried in the enzyme electrode in molding.

On the other hand, the mixture can be printed by squeezing after the mixture is applied in a state where a mask is placed on the print media having a smooth plane, for example. The printing thickness is suitably set according to the use of the enzyme electrode, or the like. The thickness is made to be 5 to 500 μm, for example. The enzyme electrode is obtained by evaporating the liquid suspension medium by drying after printing the mixture.

The print media having, for example, a film shape and a plate shape is used. The enzyme electrode may be exfoliated from the print media and be used. The enzyme electrode can be also used while the enzyme electrode is supported by the print media. In the case of the latter, the print media functions as the supporting member. The print media may have a concave part formed in the printing part of the mixture. In this case, the mask can be omitted.

The redox enzyme may not necessarily be added into the mixture. For example, the redox enzyme may be fixed by impregnating a formed body or a printing film with an enzyme solution after molding the mixture containing the metal particle and the high-resistance particle or after forming a printing film, and by drying the formed body or the printing film.

After a suspension prepared without adding the binder is dried and made as a powder state, the binder may be added into this powder. In this case, the powder can be made as a paste state having viscosity suitable for printing by adding the binder.

As a matter of course, it is necessary to dry in manufacturing at a temperature lower than the temperature in which the substantial inactivation of the enzyme is generated.

Basically, the enzyme electrode of the present invention can be formed by only simple processes such as formation, molding and drying of the mixture. That is, a high mass production technique can be used, and the manufacturing cost can be desired to be reduced to such an extent that a disposable enzyme electrode can be manufactured.

As described above, when a GDH platinized carbon enzyme electrode is used as an anode electrode, and voltammetric measurement or amperometric measurement is carried out using glucose of an enzyme ground substance as a measured object, output characteristics are different whenever a measurement sensor using a GDH platinized carbon enzyme electrode is preproduced to cause low (not stabilized) reproducibility.

The present inventors examined whether unstable output characteristics were caused. As a result, the present inventors determined that the platinized carbon enzyme electrode had a latent function as the battery. That is, the present inventors found that the cause was based on the followings. A platinum particle (metal particle) held on the surface of the carbon particle became a catalyst, and electron transfer between glucose, GDH and the platinum particle progressed spontaneously to form a biofuel cell using glucose as fuel. That is, the present inventors found that the electromotive force was promptly generated according to the concentration of glucose as the measured object, and the electromotive force negatively affected on voltage sweeping and voltage applying in the voltammetric measurement and amperometric measurement of a measurement sensor. Furthermore, the present inventors found that the unstable electromotive force was also based on the following. This electromotive force promptly generated according to the glucose concentration carries out the Nernst response to the glucose concentration. However, the electromotive force was generated also except glucose in a sample, thereby causing more change elements of the electromotive force except the glucose concentration.

On the other hand, the enzyme electrode of the present invention contains the high-resistance particle, and the voltage of the battery when the current flows (in loading) is reduced as much as possible by increasing consciously the voltage drop loss in the path in which the electrons are transmitted to the electrode. That is, the enzyme electrode of the present invention consumes the electromotive force in a cell reaction which may be caused by the oxidation reaction of the ground substance using the metal particle such as platinum as the catalyst in the internal resistance of the electrode. That is, the enzyme electrode of the present invention suppresses the instability of the electrode output by using IR drop like phenomenon caused by enhancing the internal resistance.

On the other hand, when the kind and addition amount of the high-resistance particle are suitably set, the electron transfer ability between the ground substance, the enzyme and the platinum particle (metal particle) can be efficiently held, and the voltammetric measurement and the amperometric measurement can be appropriately carried out. Thereby, output characteristics are kept constant while an advantage having no use for an electron mediator as the feature of the enzyme electrode containing the carbon particle holding the metal particle having catalyst ability and a redox enzyme is enjoyed. It becomes possible to appropriately carry out the voltammetric measurement and the amperometric measurement.

Next, the present invention will be described with reference to the following examples. The present invention is not limited to the following examples.

EXAMPLE 1

In this example, the influence of the blending amount of the high-resistance particle to the resistance value of the enzyme electrode will be examined.
(Production of Enzyme Electrode)

In the production of the enzyme electrode, first, aluminum oxide ("AEROSIL"; manufactured by Degussa AG) and platinized carbon ("IFPC40-II"; manufactured by ISHIFUKU Metal Industry Co., Ltd.) were extracted so that the addition rates thereof are respectively changed and the total amount became 60 mg and were fully mixed to produce a mixed powder. Next, 1000 μL of a GDH solution of 1250 U/mL was added into the mixed powder, and they were mixed to prepare a mixed solution. The mixed solution was left at rest for 6 hours to preliminarily adsorb GDH on platinized carbon, and centrifuged to remove a supernatant fluid. A slurry after the supernatant fluid was removed was powdered by vacuum drying, and 100 μL of liquid paraffin was added into the powder. They were mixed well to produce a paste. This paste was stuffed into a base electrode (manufactured by BAS Company) having a diameter of 3 φ and producing a paste electrode, and was compressed so that the thickness was set to 2 mm by a JURACON rod to produce an electrode.
(Measurement of Resistance Value)

The resistance value was measured as resistance between a connector part and a 3 φ central part in a GDH platinized carbon enzyme electrode by a digital tester. The resistance values were measured in an air release atmosphere having an environmental temperature of 25° C. Table 1 shows the measurement results of the resistance values. As is apparent from Table 1, the resistance can be controlled in a wide range of 30Ω to 200 kΩ by the composition of aluminum oxide (AEROSIL).

TABLE 1

| | Blending ratio (platinized carbon:aluminum oxide) | | | |
|---|---|---|---|---|
| | 10:0 (60 mg: 0 mg) | 5:1 (50 mg: 10 mg) | 1:1 (30 mg: 30 mg) | 1:5 (10 mg: 50 mg) |
| Resistance value | 30Ω | 200Ω | 30 kΩ | 200 kΩ |

EXAMPLE 2

In the example, electric generating capacity as a glucose fuel cell was evaluated for a GDH platinized carbon enzyme electrode.

The electric generating capacity was evaluated by immersing an enzyme electrode as an anode electrode, and a platinum electrode as a cathode electrode into an electrolyte solution to form a battery. The electric generating capacity was measured in an air release atmosphere with a temperature of the battery set to 25° C.

Four kinds (one kind is aluminum oxide free) of enzyme electrodes having a different blending ratio of platinized carbon and aluminum oxide were produced as in example 1. The enzyme electrode has a diameter of 3 φ and a thickness of 2 mm. As the platinum electrode, a wire platinum electrode having a diameter of 1 φ and a length of 5 cm was used.

An electrolyte capacity was set to 10 mL using a phosphoric acid buffer (pH: 6.0) of 100 mmol/L as the electrolyte solution. Glucose was dissolved in the electrolyte solution so that the concentration was set to 40 mmol/L.
(Evaluation Result)

In the battery using the enzyme electrode into which aluminum oxide (AEROSIL) was not added, a large current of a current density of 30 μA/cm$^2$ at a voltage of 0.26 V was taken out. A potential difference between an anode and a cathode is 0.46 V in an open circuit, and a comparatively high voltage was obtained. This fact shows that the biofuel cell using glucose as fuel is constituted.

On the other hand, in the battery using the enzyme electrode into which aluminum oxide (AEROSIL) was added, the potential difference between an anode and a cathode in the open circuit is set to 0.3 V to 0.02 V. The potential difference of the battery is smaller than that of the battery using the enzyme electrode into which aluminum oxide (AEROSIL) is not added. It was confirmed that the potential difference became smaller when the addition amount of the aluminum oxide (AEROSIL) became larger.

In the battery using the enzyme electrode into which aluminum oxide (AEROSIL) was added, a voltage drop happened rapidly in loading (closed circuit), and a current could be hardly taken out. That is, sufficient power generation was not made in the battery using the enzyme electrode into which aluminum oxide (AEROSIL) was added. From this result, it can be said that the function as the fuel cell succeeds in being reduced by adding aluminum oxide (AEROSIL) into the enzyme electrode. That is, IR drop phenomenon was usually derived from the resistance of a solution. However, as shown in the result of this example, the IR drop phenomenon was found to be also derived from the resistance of the whole electrode.

EXAMPLE 3

In this example, the dependency of the glucose concentration of the measured current value for each of the enzyme electrode into which aluminum oxide was added and the enzyme electrode into which aluminum oxide was not added was evaluated.

The glucose concentration was adjusted by calculating so that the glucose concentration became the aimed concentration to the electrolyte solution used in example 2, and dissolving glucose. The aimed concentration was set to 0 mg/dL, 50 mg/dL, 100 mg/dL, 200 mg/dL, 400 mg/dL, 600 mg/dL and 800 mg/dL.

A current value was measured as a response value when applying voltage between the enzyme electrode and the platinum electrode by a linear sweep voltammetrical method.

Three kinds of enzyme electrodes (one kind is aluminum oxide free) having a different blending ratio of the platinized carbon and aluminum oxide were produced as in example 1. Both the enzyme electrode and the platinum electrode had a diameter of 3 φ and a thickness of 2 mm. As the platinum electrode, a wire platinum electrode having a diameter of 1 φ and a length of 5 cm was used.

A voltage was linearly swept from 0 to 1000 mV at a speed of 100 mV/sec in an anode direction. FIG. 1 showed the measurement results of the current values as results when the voltage is 400 mV.

As shown in FIG. 1, the glucose concentration dependency was not observed in the enzyme electrode into which aluminum oxide (AEROSIL) is not added. As can be seen from example 2, this is considered that the electromotive force as the fuel cell is generated in each glucose concentration, and the glucose concentration dependency is not generated by instabilizing a voltage applying state in voltammetry. That is, measurement conditions are different each time in the glucose concentrations, and thereby the result of the voltammetry is considered to be caused by the shift in the voltage direction.

On the other hand, in the enzyme electrode into which aluminum oxide (AEROSIL) was added, the glucose concentration dependency was confirmed according to the addition amount thereof. This is considered that the IR drop like phenomenon derived from the internal resistance of the enzyme electrode is generated at the moment a current flowed as could be seen from the results of example 2 in the enzyme electrode into which aluminum oxide (AEROSIL) was added, the electromotive force generated by each glucose concentration is substantially canceled, and the electron transfer ability between the ground substance, the enzyme and the platinum particle was efficiently used by satisfying the real measurement condition in each glucose concentration to confirm the glucose concentration dependency.

The absolute sensitivity tends to be reduced with the increase of the resistance caused by adding particles having a large electrical resistance and being chemically inactive such as aluminum oxide (AEROSIL) in the enzyme electrode into which highly oxidized aluminum (AEROSIL) was added. However, the absolute sensitivity can be considered to be a level having no practical problem.

EXAMPLE 4

In the example, the dependency of the glucose concentration of the measured current value was evaluated for each of the enzyme electrode to which a high resistance powder was added and the enzyme electrode to which a high resistance powder was not added.

The glucose concentration was adjusted to 0 mg/dL, 50 mg/dL, 100 mg/dL, 200 mg/dL, 400 mg/dL, 600 mg/dL and 800 mg/dL as in example 3.

The enzyme electrode was basically produced as in example 1. However, there were produced three kinds of enzyme electrodes of an enzyme electrode obtained by adding aluminum oxide (AEROSIL) as a high resistance powder, an enzyme electrode obtained by adding a high resistance object powder primarily containing silicate ("smectite"; manufactured by Co-op Chemical Co., Ltd.), and an enzyme electrode containing no high resistance powder. The blending amount of the high resistance powder was 30 mg of an equivalent amount of the platinized carbon.

Figure 2A:
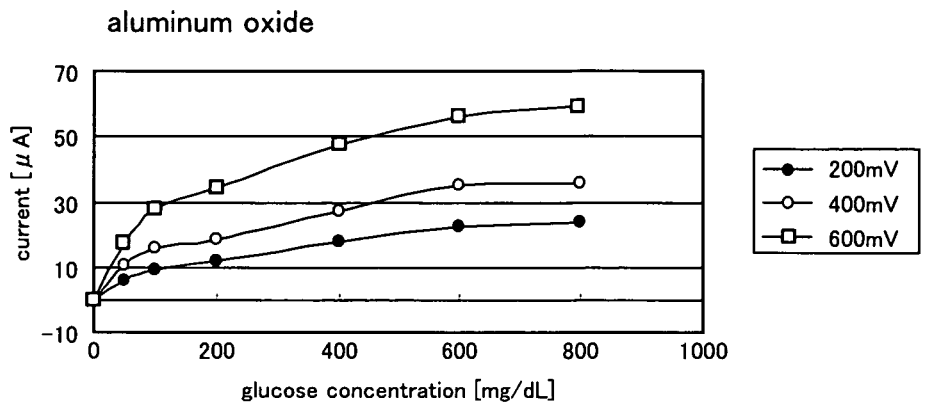
FIG. 2A is a graph showing the measurement results of current values when an enzyme electrode containing aluminum oxide in example 4 is used.
Figure 2B:
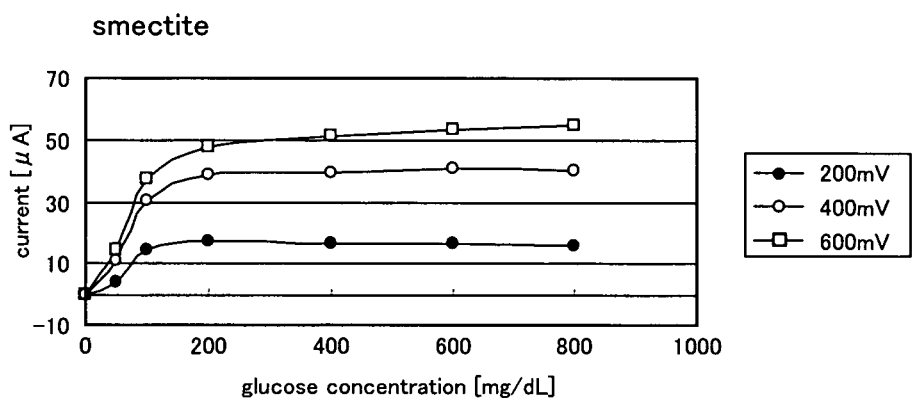
FIG. 2B is a graph showing the measurement results of current values when an enzyme electrode containing smectite is used.
Figure 2C:
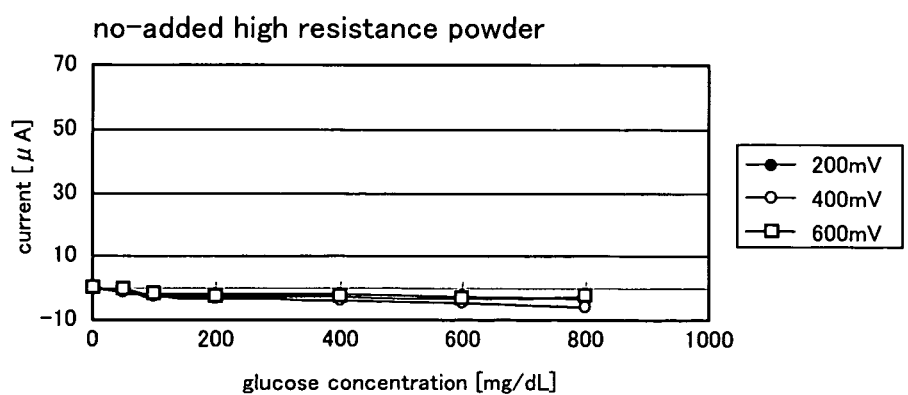
FIG. 2C is a graph showing the measurement results of current values when an enzyme electrode containing no high-resistance particle is used.

The current value was measured as in example 3 as a response value when applying voltage by the linear sweep voltammetrical method between the enzyme electrode and the platinum electrode. FIGS. 2A to 2C show the measurement results of the current values as a value when the applied voltage is 400 mV. FIG. 2A shows the measurement results of an enzyme electrode to which aluminum oxide (AEROSIL) is added. FIG. 2B shows the measurement results of an enzyme electrode when smectite primarily containing silicate is added. FIG. 2C shows the measurement results of an enzyme electrode when a high resistance powder is not added.

As shown in FIGS. 2A, 2B, the glucose concentration dependency was confirmed as in the case of example 3 in the enzyme electrode obtained by adding a high resistance powder such as aluminum oxide (AEROSIL) and smectite primarily containing silicate.

On the other hand, as shown in FIG. 2C, the glucose concentration dependency was not confirmed in the enzyme electrode to which the high resistance powder was not added. On the contrary, even if the glucose concentration became large, the current value tends to be reduced. This result is greatly different from the result of example 3. In view of this, it can be confirmed that the output is not stabilized in the enzyme electrode to which the high resistance powder is not added and the reproducibility is poor.

From the above results, the concentration dependency to glucose for the measurement current value was confirmed in the enzyme electrode obtained by adding aluminum oxide (AEROSIL) and smectite primarily containing silicate as the high resistance powder, and it was confirmed that the glucose concentration can be appropriately measured.

The invention claimed is:

1. An enzyme electrode comprising:
   a carbon particle;
   a metal particle held on the carbon particle, the metal particle having a catalytic activity against a redox reaction;
   a redox enzyme; and
   a high-resistance particle enhancing an electrical resistance, the high-resistance particle being chemically stable,
   wherein the high-resistance particle creates electrical resistance of the enzyme electrode equal to or more than about 30 k$\Omega$, and
   wherein the high-resistance particle has a particle size of 3 to 150 nm.

2. An enzyme electrode comprising:
   a carbon particle;
   a metal particle held on the carbon particle, the metal particle having a catalytic activity against a redox reaction;
   a redox enzyme; and
   a high-resistance particle enhancing an electrical resistance, the high-resistance particle being chemically stable,
   wherein the high-resistance particle creates electrical resistance of the enzyme electrode equal to or more than about 30 k$\Omega$, wherein the high-resistance particle contains an inorganic substance,
wherein the inorganic substance is silicate, or primarily contains the silicate,
wherein the inorganic substance is a clay mineral, and
wherein the clay mineral is smectite.

3. The enzyme electrode according to claim 1, wherein the high-resistance particle contains an inorganic substance.

4. The enzyme electrode according to claim 3, wherein the inorganic substance is aluminum oxide.

5. The enzyme electrode according to claim 3, wherein the inorganic substance is a hydrophilic fumed alumina.

6. The enzyme electrode according to claim 3, wherein the inorganic substance is silicate, or primarily contains the silicate.

7. The enzyme electrode according to claim 6, wherein the inorganic substance is a clay mineral.

8. The enzyme electrode according to claim 1, wherein the metal particle contains a noble metal.

9. The enzyme electrode according to claim 8, wherein the noble metal is at least one selected from the group comprising of platinum (Pt), rhodium (Rh), gold (Au), silver (Ag), palladium (Pd), ruthenium (Ru), iridium (Ir) and osmium (Os).

10. The enzyme electrode according to claim 9, wherein the noble metal is platinum (Pt).

11. The enzyme electrode according to claim 1, wherein the metal particle has a particle size of 1 to 4 nm.

12. The enzyme electrode according to claim 1, wherein the carbon particle has a particle size of 3 to 150 nm.

13. The enzyme electrode according to claim 1, wherein the redox enzyme is a glucose dehydrogenase.

14. The enzyme electrode according to claim 13, wherein the glucose dehydrogenase is a glucose dehydrogenase (FADGDH) containing flavin adenine dinucleotide (FAD) as a coenzyme.

15. The enzyme electrode according to claim 1, further comprising a binder for bonding the carbon particle.

16. The enzyme electrode according to claim 15, wherein the binder contains a petroleum wax or a fluorine sulfonic acid polymer.

17. The enzyme electrode according to claim 16, wherein the petroleum wax is at least one selected from the group comprising of a paraffin wax, a microcrystalline wax and petrolatum.

18. The enzyme electrode according to claim 17, wherein the petroleum wax is the paraffin wax.

19. The enzyme electrode according to claim 16, wherein the fluorine sulfonic acid polymer is a sulfonated tetrafluoroethylene-based polymer.

20. The enzyme electrode according to claim 7, wherein the clay mineral is smectite.

* * * * *